(12) United States Patent
Balaban et al.

(10) Patent No.: US 11,419,493 B2
(45) Date of Patent: Aug. 23, 2022

(54) METHOD AND APPARATUS FOR MTBI DIAGNOSIS IMPLEMENTING EYE MOVEMENT AND PUPIL MOVEMENT ANALYSIS IN OBJECTIVE VERGENCE TESTING

(71) Applicants: Neuro Kinetics, Inc., Pittsburgh, PA (US); University of Pittsburgh—Of the Commonwealth System of Higher Education, Pittsburgh, PA (US); University of Miami, Miami, FL (US)

(72) Inventors: Carey D. Balaban, Pittsburgh, PA (US); Mikhaylo Szczupak, Miami, FL (US); Michael E. Hoffer, San Diego, CA (US); Robin C. Ashmore, Pittsburgh, PA (US); Alexander Kiderman, Pittsburgh, PA (US)

(73) Assignees: NEURO KINETICS, INC & UNIVERSITY OF PITTSBURGH, Pittsburgh, PA (US); UNIVERSITY OF MIAMI, Miami, FL (US)

( * ) Notice: Subject to any disclaimer, the term of this patent is extended or adjusted under 35 U.S.C. 154(b) by 483 days.

(21) Appl. No.: 15/897,137

(22) Filed: Feb. 14, 2018

(65) Prior Publication Data
US 2018/0242842 A1 Aug. 30, 2018

Related U.S. Application Data

(60) Provisional application No. 62/458,876, filed on Feb. 14, 2017.

(51) Int. Cl.
*A61B 3/113* (2006.01)
*A61B 3/14* (2006.01)
(Continued)

(52) U.S. Cl.
CPC ............. *A61B 3/113* (2013.01); *A61B 3/005* (2013.01); *A61B 3/0091* (2013.01); *A61B 3/08* (2013.01);
(Continued)

(58) Field of Classification Search
CPC . A61B 3/11; A61B 3/111; A61B 3/112; A61B 3/113; A61B 3/005; A61B 3/0091;
(Continued)

(56) References Cited

U.S. PATENT DOCUMENTS 8,568,311 B2  10/2013  LaPlaca et al.
8,585,609 B2  11/2013  Kiderman et al.
(Continued)

FOREIGN PATENT DOCUMENTS

WO  WO 2017/147141  8/2017

OTHER PUBLICATIONS

Christopher W. Tyler, Lora T. Likova, Kristyo N. Mineff, Anas M. Elsaid, Spero C. Nicholas, Consequences of Traumatic Brain Injury for Human Vergence Dynamics, Published online Feb. 3, 2015. doi: 10.3389/fneur.2014.00282, https://www.ncbi.nlm.nih.gov/pmc/articles/PMC4315029/.
(Continued)

*Primary Examiner* — Daniel L Cerioni
*Assistant Examiner* — Deirdre M Willgohs
(74) *Attorney, Agent, or Firm* — Blynn L. Shideler; Krisanne Shideler; BLK Law Group

(57) ABSTRACT

An objective screening platform for mTBI screening includes a vergence testing stimulus generator visible to a subject and configured for presenting visual stimulus to a subject which forms an optical target stimulus for at least one vergence test; at least one data acquisition unit for obtaining objective physiologic responses of the subject unit based upon each of the visual stimulus presented to the
(Continued)

subject in each test, wherein the objective physiologic responses for each test include at least one eye position parameter and at least one pupil area parameter; and a controller configured for using at least one eye position parameter and at least one pupil area parameter to screen for the presence of mTBI of the subject.

16 Claims, 4 Drawing Sheets

(51) Int. Cl.
*A61B 3/11* (2006.01)
*A61B 3/00* (2006.01)
*A61B 5/00* (2006.01)
*A61B 5/12* (2006.01)
*A61B 3/08* (2006.01)
*A61B 90/50* (2016.01)

(52) U.S. Cl.
CPC .............. *A61B 3/112* (2013.01); *A61B 3/145* (2013.01); *A61B 5/123* (2013.01); *A61B 5/4064* (2013.01); *A61B 2090/502* (2016.02)

(58) Field of Classification Search
CPC ......... A61B 3/08; A61B 3/145; A61B 5/4064; A61B 5/163; A61B 5/165; A61B 5/168
USPC ......................................................... 600/558
See application file for complete search history.

(56) References Cited

U.S. PATENT DOCUMENTS

| | | | |
|---|---|---|---|
| 9,039,631 B2 | 5/2015 | Kiderman et al. | |
| 9,039,632 B2 | 5/2015 | Kiderman et al. | |
| 2010/0028037 A1 | 2/2010 | Song | |
| 2010/0094161 A1 | 4/2010 | Kiderman et al. | |
| 2014/0192326 A1 | 7/2014 | Kiderman et al. | |
| 2014/0327880 A1 | 11/2014 | Kiderman et al. | |
| 2015/0335278 A1 | 11/2015 | Ashmore et al. | |
| 2016/0213301 A1 | 7/2016 | Port | |
| 2016/0262608 A1* | 9/2016 | Krueger | G16H 50/30 |
| 2016/0270711 A1 | 9/2016 | Ashmore et al. | |
| 2017/0007119 A1* | 1/2017 | Cornsweet | A61B 3/112 |
| 2018/0279948 A1* | 10/2018 | Medberry | A61B 3/0008 |

OTHER PUBLICATIONS

Tara L. Alvarez, PhD, Eun H. Kim, PhD, Vincent R. Vicci, OD, Sunil K. Dhar, PhD, Bharat B. Biswal, PhD, and A. M. Barrett, MD, Concurrent Vision Dysfunctions in Convergence Insufficiency with Traumatic Brain Injury, Optom Vis Sci. Dec. 2012; 89(12): 10.1097/OPX.0b013e3182772dce. doi: 10.1097/OPX.0b013e3182772dce, https://www.ncbi.nlm.nih.gov/pmc/articles/PMC3826444/, Dec. 1, 2013.

Thiagarajan P , Ciuffreda KJ, Ludlam DP., Vergence dysfunction in mild traumatic brain injury (mTBI): a review., PubMed PMID: 21410499 DOI: 10.1111/j.1475-1313.2011.00831.x, https://www.ncbi.nlm.nih.gov/pubmed/21410499, Sep. 31, 2011, Abstract Only.

Carey Balaban , Michael E. Hoffer , Mikhaylo Szczupak, Hillary Snapp, James Crawford, Sara Murphy,Kathryn Marshall, Constanza Pelusso, Sean Knowles, Alex Kiderman, Oculomotor, Vestibular, and Reaction Time Tests in Mild Traumatic Brain Injury, PLOS One Tenth Anniversary, https://journals.plos.org/plosone/article?id=10.1371/journal.pone.0162168, Sep. 21, 2016.

* cited by examiner

Eye Movements and Pupil Movements
(half cycle parameter estimates by LS regression)

| Session | N | Component | Direction | Magnitude (±SE) | $R^2$ (±SE) |
|---|---|---|---|---|---|
| Control | 52 | Vergence angle | Toward | 2.537 ± 0.110° | 0.933 ± 0.088 |
| | | | Away | 2.258 ± 0.100° | |
| | | Pupil area | Toward | 23.538 ± 1.574% | 0.563 ± 0.198 |
| | | | Away | 13.428 ± 1.955% | |
| Acute | 17 | Vergence angle | Toward | 1.745 ± 0.193° | 0.652 ± 0.316 |
| | | | Away | 1.864 ± 0.175° | |
| | | Pupil area | Toward | 14.705 ± 2.752% | 0.378 ± 0.247 |
| | | | Away | 7.798 ± 3.419% | |
| Subacute (2w) | 14 | Vergence angle | Toward | 2.628 ± 0.212° | 0.931 ± 0.101 |
| | | | Away | 2.338 ± 0.192° | |
| | | Pupil area | Toward | 17.516 ± 3.033% | 0.528 ± 0.235 |
| | | | Away | 12.495 ± 3.768% | |

FIG. 4

Logistic Regression for Session 1 versus Control

| Observed Group | Control (Predicted) | mTBI (Predicted) | Percent Correct |
|---|---|---|---|
| Control | 49 | 3 | 94.2% |
| mTBI | 6 | 11 | 64.7% |
| Overall Percentage | | | 87.0% |

| | B | SE | Wald | df | Signif | Exp(B) |
|---|---|---|---|---|---|---|
| Detrended Data Slope | 0.257 | 0.099 | 6.715 | 1 | 0.010 | 1.293 |
| Vergence Fit R squared | -13.445 | 3.873 | 12.049 | 1 | 0.001 | 0.00 |
| Constant | 12.182 | 3.819 | 10.178 | 1 | 0.001 | 195226.0 |

FIG. 5

Linear Segments Showing Vergence Angle-Pupil Area Slope

| Mean ± Standard Error | Control (n=52) | Acute mTBI (n=17) | 2 week post-mTBI (n=17) |
|---|---|---|---|
| Average Slope (and $R^2$) of Detrended Relationship: % pupil area per degree convergence (weighted by sample number) | -7.94 ± 0.59 (0.456 ± 0.031) | -5.26 ± 1.02 (0.234 ± 0.055) | -5.95 ± 1.17 (0.423 ± 0.063) |
| Proportion of Sample Points Showing Negative Linear Relationship | 0.828 ± 0.015 | 0.729 ± 0.026 | 0.752 ± 0.029 |
| Average slope (and $R^2$) of linear segments with negative slope (weighted by number of samples) | -13.28 ± 0.61 (0.660 ± 0.019) | -11.79 ± 1.07 (0.591 ± 0.033) | -12.91 ± 1.23 (0.682 ± 0.038) |

FIG. 6

METHOD AND APPARATUS FOR MTBI DIAGNOSIS IMPLEMENTING EYE MOVEMENT AND PUPIL MOVEMENT ANALYSIS IN OBJECTIVE VERGENCE TESTING

RELATED APPLICATIONS

This application claims the benefit of U.S. Patent Application 62/458,876 filed Feb. 14, 2017 entitled "Analysis of Eye and Pupil Movement Coordination in Vergence Testing for Detection of Acute mTBI."

BACKGROUND OF THE INVENTION

1. Field of the Invention

The present invention relates to mTBI diagnosis implementing eye movement and pupil movement analysis in objective vergence testing.

2. Background Information

Traumatic Brain Injury (TBI) is the result of a blunt blow, jolt or blast overpressure to the head that disrupts brain function. The subset of mild TBI, or mTBI, has represented a harder segment of TBI to diagnose. Within this application mTBI is a subset of TBI, although within this application a method and apparatus for mTBI Diagnosis is also inclusive of a method and apparatus for TBI diagnosis. The terms mild TBI (mTBI) and concussion are commonly used interchangeably in the art, and have been linked with Post Traumatic Stress Disorder. mTBI is a heterogeneous condition with diverse clinical presentations. The severity of head injuries range from a brief change in mental status or consciousness to extended unconsciousness and amnesia. In severe or multiple concussion cases, personality changes can occur with devastating results.

The Centers for Disease Control and Prevention previously estimated that at least 3.17 million Americans currently have a long-term or lifelong need for help to perform activities of daily living as a result of a TBI. Currently there are few accepted clinical methods to detect mTBI. The Center for Disease Control estimates that "About 75% of TBIs that occur each year are concussions or other forms of mild TBI." For further background please see Brain Injury Association of America at www.BIAUSA.org as The Brain Injury Association of America (BIAA) is the country's oldest and largest nationwide brain injury advocacy organization.

Proper treatment of TBI injury requires an accurate diagnosis of the structures affected. Neurosensory symptoms, including oculomotor and vestibular (dizziness and balance) disorders, are among the most common disabilities seen after injury. Proper treatment of TBI injury requires an accurate diagnosis of the structures affected. The mechanisms of injury in TBI cause a variety of abnormalities in the peripheral vestibular mechanisms, central vestibular structures, ocular-motor tracts, cerebellum, as well as all portions of the brain communicating with these structures. Despite their prevalence, these symptoms and deficits can be difficult to quantify.

Existing screening and diagnostic tools for mTBI in general which are employed on patients and which are based on the traditional battery of vestibular, balance and neurological tests often requires the use of large stationary systems (neuro-otologic test center, Barany/rotary chair, ENG/VNG, computerized posturography/balance platforms, etc.). These large systems deploy a full battery of ocular motor, motion, artificial motion, balance and combined tests. Utilizing such devices may be practical in hospital settings, but are not useful in forward deployed military settings, or remote locations, such as first responder emergency medical technicians (EMTs).

In the work published as, Balaban C, Hoffer M E, Szczupak M, Snapp H, Crawford J, Murphy S, et al. (2016) *Oculomotor, Vestibular, and Reaction Time Tests in Mild Traumatic Brain Injury*; PLoS ONE 11(9): e0162168; researchers looked at a battery of testing for mTBI. In this review two cohorts each of fifty subjects with mild traumatic brain injury and one hundred controls were evaluated with a battery of oculomotor, vestibular and reaction time related tests applied to a population of individuals with mild traumatic brain injury as compared to controls. This research demonstrated pattern differences between the two groups and showed how three of these tests yield an 89% sensitivity and 95% specificity for confirming a current diagnosis of mild traumatic brain injury. These results help better characterize the oculomotor, vestibular, and reaction time differences between those the mild traumatic brain injury and non-affected individuals. This characterization suggested the need for the development of more effective point of care neurologic diagnostic techniques and suggested the need for more targeted treatment which may allow for quicker return to normal activity.

For further background on TBI assessment systems consider U.S. Pat. No. 8,568,311 developed by Emory University which discloses an immersive cognitive assessment system which suppresses outside video and audio inputs. Additionally of interest is publication number 2016/0213301 developed by Indiana University a portable eye movement monitoring system for TBI detection. The '311 patent and the 301 publication, which are incorporated herein by reference, are helpful to further establish the state of the art.

Additionally Neurokinetic, Inc., (NKI) one of the applicants of this application, has developed noninvasive rapid screening of mild traumatic brain injury using combination of subject's objective oculomotor, vestibular and reaction time analytic variables set forth in publication number 2015-0335278. See also Publication No. 2016-0270711, Publication No. 2014-0327880 and related U.S. Pat. No. 9,039,632; Publication No. 2014-0192326 and related U.S. Pat. No. 9,039,631; and U.S. Publication Number 2010-0094161 and related U.S. Pat. No. 8,585,609, each of which patents and publications are incorporated herein by reference.

Vergence is an oculomotor function, described as disconjugate movement of the eyes to track objects varying in depth over the binocular visual field, and is commonly affected following mTBI. Convergence insufficiency, determined by static measures of vergence function, has long been known to result from mTBI specifically a receded near point of convergence amplitude; a decreased compensatory fusional ranges at near; and abnormal phoria at near or far (horizontal, vertical). See Thiagarajan P, Ciuffreda K J, Ludlam D P" *Vergence dysfunction in mild traumatic brain injury (mTBI): a review*; Ophthalmic Physiol Opt. 2011 September; 31(5):456-68. doi: 10.1111/j.1475-1313.2011.00831.x. Epub 2011 Mar. 16; which presents a review of the vergence system and its anomalies in mild traumatic brain injury, as well as their diagnostic and therapeutic clinical ramifications, and this helpful background paper also considers the implications related to brain imaging and human neuroplasticity. Additionally see also the 2012 publication by Tara L. Alvarez, PhD, Eun H. Kim, PhD, Vincent R. Vicci, O D, Sunil K. Dhar, PhD, Bharat B. Biswal, PhD, and A. M. Barrett, M D; *Concurrent Vision Dysfunctions in Convergence Insufficiency with Traumatic Brain Injury*; Optom Vis Sci. 2012 December; 89(12): 10.1097/OPX.0b013e3182772dce.doi: 10.1097/OPX.0b013e3182772dce which assessed the prevalence of convergence insufficiency (CI) with and without simultaneous vision dysfunctions within the traumatic brain injury (TBI) sample population. Further see Christopher W. Tyler, Lora T. Likova, Kristyo N. Mineff, Anas M. Elsaid, and Spero C. Nicholas; *Consequences of Traumatic Brain Injury for Human Vergence Dynamics*; Front Neurol. 2014; 5: 282, Published online 2015 Feb. 3. doi: 10.3389/fneur.2014.00282; in which measurements of vergence eye movement parameters were utilized to support the hypothesis that occult injury to the oculomotor control system is a common residual outcome of dTBI (referenced therein as diffuse TBI wherein traumatic brain injury was classified into focal and diffuse forms, depending on the presence or absence of an identifiable focus of damage in the brain—and thus while not exact the dTBI will analogous to the mTBI designation used herein).

It is the object of the present invention to provide an objective screening platform and associated method for mTBI screening implementing vergence testing.

SUMMARY OF THE INVENTION

The present invention is drawn to a method and apparatus for mTBI diagnosis implementing eye movement and pupil movement analysis in objective vergence testing.

One aspect of the invention provides an objective screening platform and associated method for mTBI screening comprising: a vergence testing stimulus generator visible to a subject and configures for presenting visual stimulus to a subject which forms an optical target stimulus for at least one vergence test; at least one data acquisition unit for obtaining objective physiologic responses of the subject unit based upon each of the visual stimulus presented to the subject in each test, wherein the objective physiologic responses for each test include at least one eye position parameter and at least one pupil area parameter; and a controller configured for using at least one eye position parameter and at least one pupil area parameter to screen for the presence of mTBI of the subject.

The objective screening platform and associated method for mTBI screening according to one aspect of the invention provides wherein the at least one data acquisition unit includes two cameras for recording eye movement at least at 60 Hz are configures for obtaining objective physiologic responses of the subject unit based upon each of the visual stimulus presented to the subject. The vergence testing stimulus generator may further include a VR screen configured to present visual stimulus to the subject. The controller may be formed as part of a laptop wherein a head mounted goggle based stimulus generating eye tracking unit is coupled to the laptop, and wherein the unit including the VR screen and the two cameras for recording eye movement.

The objective screening platform for mTBI screening according to one aspect of the invention may provide wherein the visual stimulus presented to the subject includes a monocular stimulus moving sinusoidally toward and away from the subject at midline at 0.1 Hz.

The objective screening platform for mTBI screening according to one aspect of the invention may provide wherein the at least one eye position parameter includes a total change of angular position of the left and right eyes of the subject throughout each test.

The objective screening platform for mTBI screening according to one aspect of the invention may provide wherein the at least one pupil area parameter includes a total change of area of the left and right eyes of the subject throughout each test.

The objective screening platform for mTBI screening according to one aspect of the invention may provide wherein the objective physiologic responses for each test include parameters for the subject while visual stimulus is moving toward the subject and parameters for the subject while visual stimulus is moving away from the subject.

The objective screening platform for mTBI screening according to one aspect of the invention may provide wherein the screening for the presence of mTBI of the subject includes evaluation of objective physiologic responses to detect depressed modulation magnitude and increased variability for ocular convergence in smooth pursuit vergence testing, and depressed modulation magnitude and increased variability for pupil constriction in smooth pursuit vergence testing The objective screening platform for mTBI screening according to one aspect of the invention may provide wherein the screening for the presence of mTBI of the subject includes evaluation of objective physiologic responses to detect diminished coordination between ocular convergence and pupil responses.

These and other advantages are described in the brief description of the preferred embodiments in which like reference numeral represent like elements throughout.

BRIEF DESCRIPTION OF THE FIGURES

FIG. 4 is a chart of the results of an analysis of eye movement and pupil movement from objective vergence testing from sets of control, acute mTBI and subacute mTBI subjects;

FIG. 5 is a chart evidencing the predictive results of implementing eye movement and pupil movement analysis in objective vergence testing; and FIG. 6 is a chart illustrating vergence angle-pupil area slope data analysis of control, acute and acute subjects two weeks after concussion event.

DESCRIPTION OF THE PREFERRED EMBODIMENTS

Figure 1:
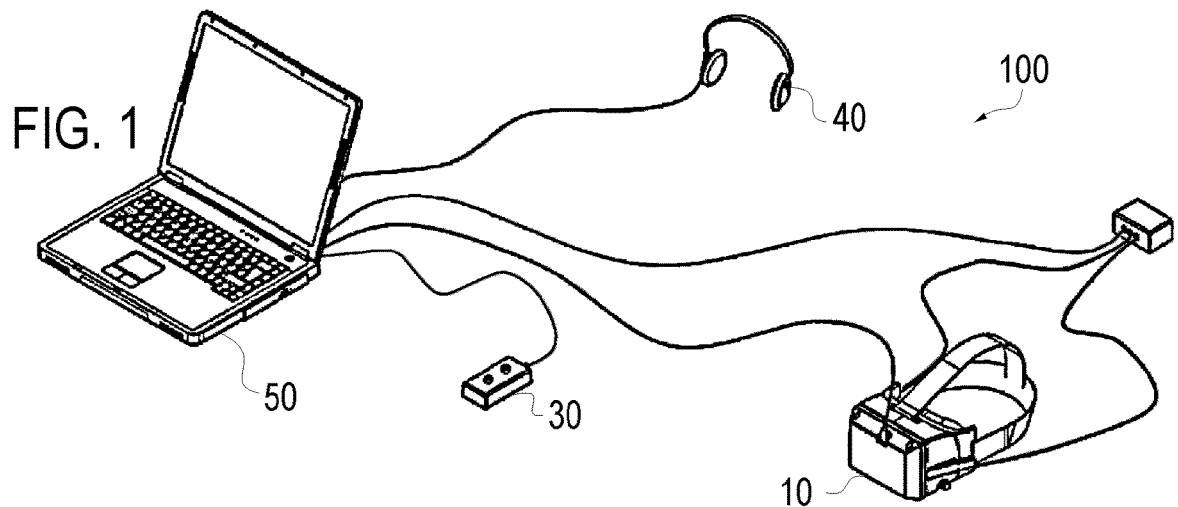
FIG. 1 is a schematic view of a dynamic vergence testing platform including 3d head mounted display system with integrated eye tracking technology for objective screening platform and associated method for mTBI screening in accordance with the present invention.

It is noted that, as used in this specification and the appended claims, the singular forms "a," "an," and "the" include plural referents unless expressly and unequivocally limited to one referent.

The present invention is drawn to a method and apparatus or platform 100 for mTBI diagnosis implementing eye movement and pupil movement analysis of the subjects eyes 120 in objective vergence testing. More precisely the apparatus or platform 100 and associated method may be described as a medical assist device to assist medical professionals in the diagnosis of mTBI and this may be described as a screening tool and method for mTBI. The apparatus or platform 100 and associated method will also assist in the diagnosis and/or screening of TBI in general, and mTBI in particular. The apparatus or platform 100 may be further combined and integrated with the implementation of other biomarkers to enhance the results, which is not intended to detract from the novel aspects of utilizing the biomarkers set forth in the apparatus or platform 100 and method as set forth below.

The platform 100 or system for mTBI diagnosis implementing eye movement and pupil movement analysis of the subject's eyes 120 in objective vergence testing of the present invention may be categorized as a type of Videooculography (VOG) system. Richard E. Gans, PhD is the Founder and Executive Director of the American Institute of Balance and he served on the board of the American Academy of Audiology. VOG systems have been defined by Richard E. Gans, PhD (*Hearing Journal*: May 2001— Volume 54—Issue 5—pp 40, 42) as follows: "Video-oculography is a method of recording eye movement through the use of digital video cameras. This is a significant change from electronystagmography, which uses the corneal retinal potential, which is the eye's battery-like effect. As the eyes move side to side and up and down, the corneo-retinal potential's positive and negative discharge is recorded. VOG technology, however, uses infrared cameras to measure the eye's position. Small cameras, mounted in goggles, track the center of the pupil to provide the location of the eye." Specifically, the platform 100 is formed on the I-Portal®— PAS (Portable Assessment System, manufactured and supported by NKI), a portable 3D head mounted display (HMD) system with integrated eye tracking technology. This technology is advantageous because it tests oculomotor and vergence function in an entirely virtual environment. Further details of this system or platform 100 and vergence testing is described in WO 2017/147141 of NKI which is incorporated herein by reference.

Videonystagmograpy (VNG) is often defined as a technology for testing inner ear and central motor functions, a process known as vestibular assessment and is defined as involving the use of infrared cameras to trace eye movements during visual stimulation and positional changes. A VNG unit is typically a diagnostic system for recording, analyzing and reporting (generally) involuntary eye movements, called nystagmus for involuntary movements, using video imaging technology. The eye tracking unit or platform 100, as described in greater detail below, may also be defined as a VNG system. VNG systems are considered, for the purpose of this application, to be a subset of the broader VOG terminology.

FIG. 1 is a schematic view of the dynamic vergence testing platform 100 or system including 3d head mounted display system 10 with integrated eye tracking technology for objective testing of vergence of the subject. The system or platform 100 includes the head mounted goggle unit 10, user input device 30 (e.g., for reaction testing inputs), headphones 40 for auditory input for instructions or stimulus and/or subject isolation, coupled to a laptop 50 to yield a highly portable system 100.

The VOG/VNG system or platform 100 is coupled to the subject and configured to present a plurality of virtual reality based visual stimulus 25 to the subject, at least one visual stimulus 25 providing a target stimulus 25 for a visual based neurologic vergence testing. The system or platform 100 is designed to obtain objective physiologic response of the subject's eyes 120 from the eye tracking unit based upon the neurologic vergence test associated with each vergence visual stimulus 25 presented to the subject, namely the objective physiologic responses for each test for this invention include at least one eye position parameter and at least one pupil area parameter. The system or platform 100 is configured to use the objective physiologic responses to the neurologic vergence tests to diagnose or screen for the presence of mild traumatic brain injury, or TBI more generically, as described below.

The VR technology in the present invention is used to provide a visual target 25 for performing at least one, and possibly a variety of vergence neurologic tests on the subject. The portable system or platform 100 has the potential of being used bedside, in the home, and in the field (e.g. at sporting events or sites of injury).

Figure 2:
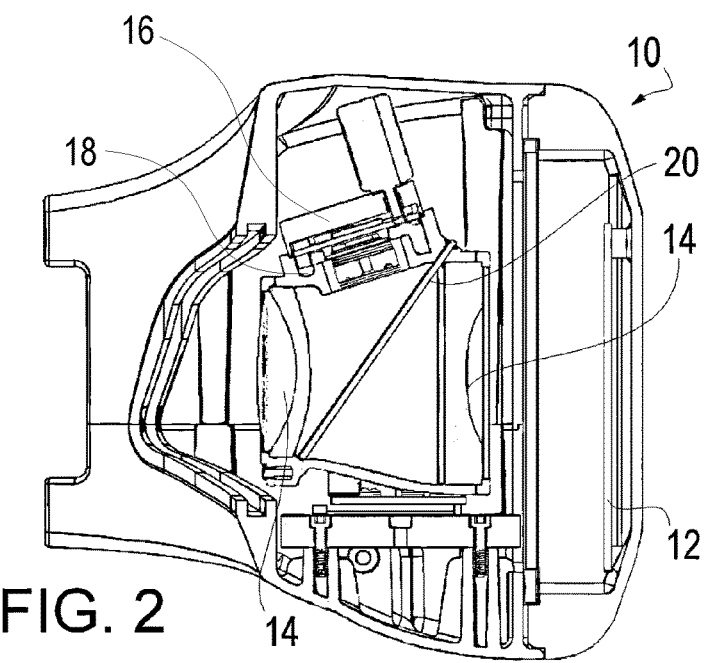
FIG. 2 is a schematic sectional view of the 3d head mounted display system of the vergence testing platform of FIG. 1.

FIG. 2 is a schematic design of head mounted VOG/VNG goggle unit 10 with OLED micro display or VR screen 12, two sets of optics 14, cameras 16 for recording eye movement typically at or above 60 hz, generally around 100 Hz or even higher for vergence testing, micro LEDs 18 for illumination of the eyes 120, and a hot mirror 20. Simply, the VR screen 12 provides the visual stimulus 25 and the cameras 16 capture eye 120 response for quick analysis. The details of the VR display screen 12 are believed to be known to those or ordinary skill in the art and it allows the system or platform 100 to present visual images or targets 25 to the user that have a perceived or simulated distance for vergence testing. The eye tracking technology described herein, outside of the vergence testing described herein, is generally known in the art, and the camera based eye tracking goggle based unit 10 may use the IPORTAL® brand goggle based eye tracking cameras and software available from NKI.

The combination of the eye tracking and the display of simulated distanced visual targets 25 allow the VOG/VNG system or platform 100 to automatically run one or more preprogrammed neurologic vergence tests and to record the physiologic responses thereto.

Figure 3:
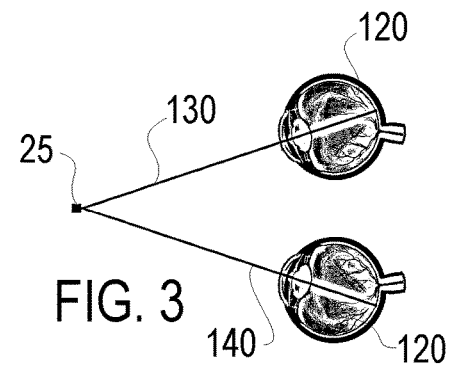
FIG. 3 schematically illustrates vergence testing physiology.

FIG. 3 schematically illustrates vergence testing physiology. The device 10 will present a pair of stimuli that combine forming target 25 to each eye 120, each stimuli controlled independently, to simulate varying depth targets 25. Targets 25 can be, for instance, single dot targets, images, or any other visual stimulus 25 capable of being rendered on the screen 12. Through the varying of the horizontal shift of each eye's targets independently, an impression of varying depth is created for the target 25 as the subject converges their eyes 120, along separate gaze tracks or lines 130, 140, on the independent targets and fuses the two images into a perceived single image or target 25. This is generally well known standard practice for creating virtual depth in a VR environment of the screen 12. The VR stimulus software for performing the tests of the present invention is integrated into existing vestibular/neurological software for protocol setup, test results analysis, and to create VR stimulus 25.

One vergence test of the method or platform 100 will present a continuously, smoothly transitioning movement of the stimuli 25, creating the appearance of a target 25 gradually moving toward or away from the subject in the virtual depth space. This will encourage subjects to make continually updated, smoothly transitioning convergence and divergence eye 120 movements. This may be referred to as "vergence pursuit test" or "vergence smooth pursuit test".

For the vergence smooth pursuit test, subjects visualized the stimulus 25 moving towards and away in a sinusoidal pattern at 0.1 Hz.

As noted above, with regard to the present invention the objective physiologic responses for each test for this invention include at least one eye position parameter and at least one pupil area parameter.

A principle eye position parameter used in the present invention is vergence angle sometimes called excursion and it is a measure of the difference between the near and far angle and may be referenced as an amplitude measurement of total eye movement. There is a vergence angle for the subjects left eye and right eye and average of both. When not differentiated vergence angel is the average of both eyes. Another vergence angle measurement is the difference between the right and left eye vergence measurement, which can also be described as a vergence angle symmetry measurement. Obtaining a vergence measurement requires the obtaining of near and far angle eye measurements, namely measures of the angle of the left and right eye with the target 25 at the nearest point and the farthest point, respectively, in its sinusoidal movement. Lag time, also known as temporal shift, is a measure of the delay between target movement and tracking eye movement and is also an eye position parameter, with lag time having average, left eye, right eye and symmetry measures. Eye angle velocity measurements are also possible eye position parameters, but may not be as meaningful for a vergence smooth pursuit test as described.

A principle pupil area parameter used in the present invention is the percentage change in pupil area. This pupil area parameter necessitates a maximum area pupil area measurement and a minimum pupil area measurement throughout the half cycle (which is discussed below). Analogous to the vergence angle, there is a change in pupil area measurement for the subjects left eye and right eye and average of both, and when not change in pupil area references the average of both eyes. Another change in pupil area measurement is the difference between the right and left eye change in pupil area measurement, which can also be described as a change in pupil area symmetry measurement.

For Vergence Pursuit testing, data will be both segmented into individual cycles of toward the subject and away from the subject with these cycles forming sub-segments of the target movement profile, e.g., cycles of a sinusoidally-modulated stimulus, and analyzed per half-cycle (toward and away). Additionally the data can be analyzed for the full cycles.

FIG. 4 is a chart of the results of an analysis of eye movement and pupil movement from objective vergence testing from sets of control, acute mTBI and subacute mTBI subjects illustrating the aspects of the present invention. As noted above the visual stimulus presented to the subjects includes a monocular stimulus moving sinusoidally toward and away from the subject at midline at 0.1 Hz. The control subjects includes 52 subjects, 36 male and 16 female between the ages of 21 and 45 years with a mean age of 28.7 years and a standard deviation of 6.3 years. The acute subjects included 17 individuals diagnosed by an emergency room physician as having mTBI and tested within 24-48 hours of injury. All subjects were tested at one of University of Miami Miller School of Medicine, Madigan Army Medical Center or the Naval Medical Center San Diego. The 17 concussed or mTBI subjects included 13 males and 4 females between the ages of 20 and 43 with a mean age of 29.1 years and a standard deviation of 8.1 years. The sub-acute subjects represent 14 of the acute subjects re-evaluated more than two weeks from the injury date. The data obtained is normalized and detrended for the half cycles and vergence angle and change in pupil area (marked as pupil area) are shown in FIG. 4. The results demonstrate a significant difference in some of the vergence angle and pupil area measurements of the acute subjects compared with the control subjects.

FIG. 5 is a chart evidencing the predictive results of implementing eye movement and pupil movement analysis in objective vergence testing. Specifically the identified difference between the vergence angle and pupil area measured between the two populations represented in FIG. 4 was used to "predict" the presence of mTBI of individual subjects based upon their individual results. Specifically an analysis of the eye and pupil movement coordination was used as a differentiating parameter as discussed further in connection with FIG. 6. The results demonstrate a relatively low false positive rate (3/52) and a meaningful predictive test 11/17 as one screening for mTBI. These results are likely to be improved with higher sample size and further implementing additional biomarkers into the analysis.

FIG. 6 is a chart illustrating vergence angle-pupil area slope data analysis of control, acute and acute subjects two weeks after concussion event. This chart illustrates examples of combining the eye movement and pupil movement data into what can be described as eye and pupil movement coordination parameters. As evidenced in the chart the measurement of % pupil area change per degree of convergance illustrates a statistically significant difference between the acute sample and the control sample as does a proportion of sample points showing negative linear relationships. Regarding the "sample points" the sampled detrended normalized pupil area and detrended vergence angles were considered as a multivariate time series and a modified Gath-Geva clustering algorithm (see Abonyi et al Fuzzy Sets and Systems 149:39-56, 2005) was used for objective fuzzy segmentation of the time series into 15 segments with homogeneous properties.

The above analysis showed that in acute mTBI subjects demonstrated depressed modulation magnitude and increased variability for ocular convergence in smooth pursuit vergence testing, and depressed modulation magnitude and increased variability for pupil constriction in smooth pursuit vergence testing, and diminished coordination between ocular convergence and pupil responses. It was also noted that performance significantly improved in the acute patients (in the 14 retested) within 2-3 weeks of injury.

Vergence deficiencies can be objectively measured and characterized using the portable, 3D head mounted display system or platform 100 with integrated eye tracking technology. Characterizing vergence function in healthy controls and pathologic dysfunction in mTBI patients as evidenced herein is an additional tool in the management and study of individuals with mTBI. Vergence data may be used as a tool in the diagnosis of mTBI and return to activity decision making.

The vergence testing on the platform 100 is not limited to the specific examples discussed above. A second vergence test is known as a Vergence Step and is formed by presenting the target 25 at different virtual depths in a punctuated fashion. This can also be described as sudden shifts in target position followed by delays where the target 25 is stationary. The present invention contemplates utilizing the objective physiologic responses for each vergence step test to include at least one eye position parameter and at least one pupil area parameter, essentially as discussed above in connection with vergence smooth pursuit testing.

A third vergence test of the present invention using platform 100 is to present either of the first two manifestations in combination with additional horizontal and/or vertical movement that will create the impression of a target 25 that moves virtually in all three dimensions. Here we refer to this form of testing as "Full 3-Dimensional Vergence". As one example instance, a test could be presented in which the target moves smoothly along a virtual trajectory through all 3 spatial dimensions, tracing a circle, ellipse, spiral, or any other trajectory that is at any angle to the visual plane, or that continuously changes angle relative to the visual plane. Again it is a critical aspect of the invention if such a Full 3-Dimensional Vergence test is used then the objective physiologic responses for each such Full 3-Dimensional Vergence test shall include at least one eye position parameter and at least one pupil area parameter, essentially as discussed above in connection with vergence smooth pursuit testing.

The above described invention provides An objective screening of mTBI comprising the steps of: presenting visual stimulus to a subject which forms an optical target stimulus for at least one vergence test; obtaining objective physiologic responses of the subject unit based upon each of the visual stimulus presented to the subject in each test, wherein the objective physiologic responses for each test include at least one eye position parameter and at least one pupil area parameter; and using at least one eye position parameter and at least one pupil area parameter to screen for the presence of mTBI of the subject.

A portable objective testing platform for vergence testing 100 may be summarized as including a laptop 50; and a head mounted goggle based stimulus generating eye tracking unit 10 coupled to the laptop 50, the unit 10 including a VR screen 12 and two cameras 16 for recording eye movement, wherein the VR screen 12 is configured to present visual stimulus 25 to the subject, wherein the visual stimulus 25 is in the head mounted goggle based system 10 and forms the optical target stimulus 25 for at least one vergence test, and wherein the cameras 16 are configured to obtain objective physiologic responses of the subject from the head mounted goggle unit 10 based upon each of the visual stimulus 25 presented to the subject in each test. This can be described as an objective screening platform for mTBI screening comprising: a vergence testing stimulus generator visible to a subject and configures for presenting visual stimulus to a subject which forms an optical target stimulus for at least one vergence test; at least one data acquisition unit for obtaining objective physiologic responses of the subject unit based upon each of the visual stimulus presented to the subject in each test, wherein the objective physiologic responses for each test include at least one eye position parameter and at least one pupil area parameter; and a controller configured for using at least one eye position parameter and at least one pupil area parameter to screen for the presence of mTBI of the subject.

It is understood, therefore, that this invention is not limited to the particular embodiments disclosed, but it is intended to cover modifications that are within the spirit and scope of the invention, as defined by the appended claims and equivalents thereto. The preferred embodiments described above are illustrative of the present invention and not restrictive hereof. It will be obvious that various changes may be made to the present invention without departing from the spirit and scope of the present invention. The precise scope of the present invention is defined by the appended claims and equivalents thereto.

What is claimed is:

1. An objective screening of mTBI comprising the steps of:
   presenting at least one visual stimulus to a subject which forms an optical target stimulus for at least one vergence test wherein the visual stimulus presented to the subject for at least one vergence test includes at least one of i) a monocular stimulus moving sinusoidally to simulate movement toward and away from the subject for smooth pursuit vergence testing, and ii) presenting the target at different simulated depths in a punctuated fashion for vergence step testing;
   obtaining objective physiologic responses of the subject based upon each of the visual stimulus presented to the subject in each vergence test, wherein the objective physiologic responses for each vergence test include at least one eye position parameter and at least one pupil area parameter, wherein the at least one pupil area parameter includes a total change of area of the left and right eyes of the subject throughout each vergence test; and
   using the at least one eye position parameter and the at least one pupil area parameter to screen for the presence of mTBI of the subject, wherein the using the at least one eye position parameter and the at least one pupil area parameter to screen for the presence of mTBI of the subject comprises detrending the at least one eye position parameter and the at least one pupil area parameter, thereby producing a multivariate time series, and applying a clustering algorithm to the multivariate time series, wherein the algorithm performs objective fuzzy segmentation.

2. The objective screening of mTBI according to claim 1, wherein two cameras for recording eye movement at least at 60 Hz are provided for obtaining objective physiologic responses of the subject based upon each of the visual stimulus presented to the subject; and wherein a VR screen is provided and is configured to present each said visual stimulus to the subject.

3. The objective screening of mTBI according to claim 2, wherein a laptop is provided with a head mounted goggle based stimulus generating eye tracking unit coupled to the laptop, the unit including the VR screen and the two cameras for recording eye movement.

4. The objective screening of mTBI according to claim 1, wherein the screening for the presence of mTBI of the subject includes evaluation of objective physiologic responses to detect abnormalities in a subject's measured vergence angle in smooth pursuit vergence testing, and abnormalities in a subject's measured pupil constriction in smooth pursuit vergence testing.

5. The objective screening of mTBI according to claim 1, wherein the visual stimulus presented to the subject includes a monocular stimulus moving sinusoidally to simulate movement toward and away from the subject at midline at 0.1 Hz.

6. The objective screening of mTBI according to claim 1, wherein the at least one eye position parameter includes a change of angular position of the left and right eyes of the subject throughout each vergence test.

7. The objective screening of mTBI according to claim 1, wherein the objective physiologic responses for each vergence test include parameters for the subject while at least one said visual stimulus is simulated moving toward the subject and parameters for the subject while at least one said visual stimulus is simulated moving away from the subject.

8. The objective screening of mTBI according to claim 1, wherein the screening for the presence of mTBI of the subject includes evaluation of objective physiologic responses to detect diminished coordination between ocular convergence and pupil responses.

9. An objective screening of vergence dysfunction of a subject comprising the steps of:
presenting at least one visual stimulus to a subject which forms an optical target stimulus for at least one vergence test, wherein the visual stimulus presented to the subject for at least one vergence test includes at least one of i) a monocular stimulus moving sinusoidally to simulate movement toward and away from the subject for smooth pursuit vergence testing, and ii) presenting the target at different simulated depths in a punctuated fashion for vergence step testing;
obtaining objective physiologic responses of the subject based upon each of the visual stimulus presented to the subject in each vergence test, wherein the objective physiologic responses for each vergence test include at least one eye position parameter, wherein the at least one eye position parameter includes a total change of angular position of the left and right eyes of the subject throughout each vergence test, and at least one pupil area parameter, wherein the at least one pupil area parameter includes a total change of area of the left and right eyes of the subject throughout each vergence test; and
using at the at least one eye position parameter and the at least one pupil area parameter to screen for the presence of vergence dysfunction of the subject, wherein the using the at least one eye position parameter and the at least one pupil area para meter to screen for the presence of vergence dysfunction of the subject comprises detrending the at least one eye position parameter and the at least one pupil area parameter, thereby producing a multivariate time series, and applying a clustering algorithm to the multivariate time series, wherein the algorithm performs objective fuzzy segmentation.

10. An objective screening platform for mTBI screening comprising:
A VR screen configured to selectively present a visual stimulus which is visible to a subject and wherein the visual stimulus forms an optical target stimulus for at least one vergence test, and the VR screen selectively displays two vergence tests including i) a smooth pursuit vergence testing wherein a monocular optical target stimulus moves sinusoidally to simulate movement toward and away from the subject, and ii) vergence step testing wherein the optical target stimulus is presented at different simulated depths in a punctuated fashion;
At least one camera recording eye movement of the subject and forming a data acquisition unit for obtaining objective physiologic responses of the subject based upon each of the visual stimulus presented to the subject in each vergence test, wherein the objective physiologic responses for each vergence test include at least one eye position parameter and at least one pupil area parameter, wherein the at least one eye position parameter includes a total change of angular position of the left and right eyes of the subject throughout each vergence test, and wherein the at least one pupil area parameter includes a total change of area of the left and right eyes of the subject throughout each vergence test; and
A computer including a controller configured for using the at least one eye position parameter including the total change of angular position and the at least one pupil area parameter including the total change of area to screen for the presence of mTBI of the subject, wherein the using the at least one eye position parameter including the total change of angular position and the at least one pupil area parameter including the total change of area to screen for the presence of mTBI of the subject comprises detrending the at least one eye position parameter and the at least one pupil area parameter, thereby producing a multivariate time series, and applying a clustering algorithm to the multivariate time series, wherein the algorithm performs objective fuzzy segmentation.

11. The objective screening platform for mTBI screening according to claim 10, wherein two of the cameras are provided for recording eye movement, each camera operating at least at 60 Hz for obtaining objective physiologic responses of the subject based upon each of the visual stimulus presented to the subject.

12. The objective screening platform for mTBI screening according to claim 11, wherein the controller is part of a laptop and wherein a head mounted goggle based stimulus generating eye tracking unit is coupled to the laptop, and wherein the unit includes the VR screen and the two cameras for recording eye movement.

13. The objective screening platform for mTBI screening according to claim 10, wherein at least one of the visual stimulus presented to the subject during smooth pursuit vergence testing is presented to the subject at midline at 0.1 Hz.

14. The objective screening platform for mTBI screening according to claim 10, wherein the objective physiologic responses for each test include parameters for the subject while at least one of the visual stimulus is simulated moving toward the subject and parameters for the subject while at least one of the visual stimulus is simulated moving away from the subject.

15. The objective screening platform for mTBI screening according to claim 10, wherein the screening for the presence of mTBI of the subject includes evaluation of objective physiologic responses to detect abnormalities in a subject's measured vergence angle in smooth pursuit vergence testing, and abnormalities in a subject's measured pupil constriction in smooth pursuit vergence testing.

16. The objective screening platform for mTBI screening according to claim 10, wherein the screening for the presence of mTBI of the subject includes evaluation of objective physiologic responses to detect diminished coordination between ocular convergence and pupil responses.

* * * * *